US008629124B2

(12) United States Patent
Soula et al.

(10) Patent No.: US 8,629,124 B2
(45) Date of Patent: *Jan. 14, 2014

(54) DEXTRAN FUNCTIONALIZED BY HYDROPHOBIC AMINO ACIDS

(75) Inventors: Gerard Soula, Meyzieu (FR); Olivier Soula, Meyzieu (FR); Remi Soula, Meyzieu (FR)

(73) Assignee: Adocia, Lyons (FR)

( * ) Notice: Subject to any disclaimer, the term of this patent is extended or adjusted under 35 U.S.C. 154(b) by 570 days.

This patent is subject to a terminal disclaimer.

(21) Appl. No.: 12/078,441

(22) Filed: Mar. 31, 2008

(65) Prior Publication Data

US 2008/0234227 A1 Sep. 25, 2008

Related U.S. Application Data

(63) Continuation-in-part of application No. PCT/IB2007/002807, filed on Sep. 26, 2007.

(60) Provisional application No. 60/907,376, filed on Mar. 29, 2007.

(30) Foreign Application Priority Data

Sep. 26, 2006 (WO) .................. PCT/IB2006/002666
Mar. 29, 2007 (FR) ...................................... 07 02316

(51) Int. Cl.
*A01N 43/04* (2006.01)
*A01N 61/00* (2006.01)
*A61K 31/715* (2006.01)
*A61K 31/00* (2006.01)

(52) U.S. Cl.
USPC .................................. 514/59; 514/54; 514/1

(58) Field of Classification Search
USPC ................................................. 514/59, 54, 1
See application file for complete search history.

(56) References Cited

U.S. PATENT DOCUMENTS

| | | | |
|---|---|---|---|
| 2,808,405 A | 10/1957 | Novak et al. | |
| 4,006,059 A | 2/1977 | Butler | |
| 4,740,594 A | 4/1988 | Mauzac et al. | |
| 5,688,931 A | 11/1997 | Nogusa et al. | |
| 5,693,625 A | 12/1997 | Barritault et al. | |
| 5,750,678 A | 5/1998 | Bauer et al. | |
| 5,977,076 A | 11/1999 | Anderson et al. | |
| 6,617,456 B1 | 9/2003 | Tsujihara et al. | |
| 6,646,120 B1 | 11/2003 | Chaubet et al. | |
| 8,241,620 B2 | 8/2012 | Dahri-Correia et al. | |
| 8,367,640 B2 | 2/2013 | Soula et al. | |
| 8,389,661 B2 | 3/2013 | Soula et al. | |
| 2004/0131583 A1 | 7/2004 | Barritault et al. | |

FOREIGN PATENT DOCUMENTS

| | | |
|---|---|---|
| DE | 41 36 324 A1 | 5/1993 |
| JP | A-60-135401 | 7/1985 |
| WO | WO 03/015826 A1 | 2/2003 |

OTHER PUBLICATIONS

Stryer, L. (1988) "Biochemistry," published by W.H. Freeman and Company, New York, p. 16-20.*
Machine translation of DE 41 36 324 A1 (published on May 13, 1993), retrieved from <http://ep.espacenet.com> on Jan. 3, 2011.*
Definition of soda, Retrieved from http://medical-dictionary.thefreedictionary.com/soda [online, retrieved on Oct. 20, 2011].*
Durand et al., "Aqueous Solutions of Native and Hydrophobically Modified Polysaccharides: Temperature Effect," *Biomacromolecules*, vol. 7, 2006, pp. 958-964.
Durand et al., "Neutral amphiphilic polysaccharides: chemical structure and emulsifying properties," *Colloid Polym. Sci.*, vol. 284, 2006, pp. 536-545.
Heinze et al., "Functional Polymers Based on Dextran," *Adv. Polym. Sci.*, vol. 205, 2005, pp. 199-291.
Jan. 9, 2013 Office Action issued in Japanese Patent Application No. 2009-528809 (with translation).
Livshits et al., "Dextran derivatives, VI. Synthesis of carboxylmethyl dextran by the azide method and the activated esters method," *Zhurnal Obshchei Khimii*, vol. 47, No. 3, 1977, pp. 699-709.
Vasil'ev et al., "N-Carboxyalkyl amides of carboxymethyl dextran," *Chemical Abstracts*, vol. 77, 1972, pp. 257-258, 105549d.
Livshits et al., "Synthesis of N-aminoacyl derivatives of carboxylmethyl dextran," *Bibliotheca Haematologica (Basel)*, No. 38, part II, 1971, pp. 770-772.
Rogovin et al., "Study of the Synthesis of Dextran Derivatives." *J. Macromol. Sci.-Chem.*, 1972, pp. 569-593.
Arranz et al., "Functionalization of dextran: Incorporation of carboxy group by O-succinoylation," *Die Angewandte Makromolekulare Chemie*, 1992, pp. 79-89.
Krentsel et al., "Kinetic Features of the Carboxymethylation of Dextran and the Structure of the Reaction Product," *Polymer Science*, Ser. A, vol. 39, No. 1, 1997, pp. 74-80.
Charpentier et al., "New hydrophobically modified carboxymethylcellulose derivatives," *Carbohydrate Polymers*, 1997, pp. 177-186.
Maiga-Revel et al., "New investigations on heparin-like derivatized dextrans: CMDBS, synergistic role of benzylamide and sulfate substituents in anticoagulant activity," *Carbohydrate Polymers*, 1997, pp. 89-93.
Office Action issued in U.S. Appl. No. 13/250,803 on May 30, 2013.
U.S. Office Action dated Sep. 24, 2013 from U.S. Appl. No. 13/250,803.

* cited by examiner

*Primary Examiner* — Scarlett Goon
(74) *Attorney, Agent, or Firm* — Oliff & Berridge, PLC

(57) ABSTRACT

The invention relates to a dextran functionalized by at least one hydrophobic alpha-amino acid radical, said alpha-amino acid being grafted or bonded to the dextran by a bonding arm and a functional group. A hydrophobic amino acid radical is understood as being the product of coupling between the amine of the amino acid and an acid carried by the bonding arm, said dextran being amphiphilic at neutral pH. In an embodiment, the hydrophobic amino acid is selected from tryptophan derivatives, such as tryptophan, tryptophanol, tryptophanamide, 2-indole ethyl-amine and their alkaline cation salts. The present invention relates also to a pharmaceutical composition comprising one of the dextrans according to the invention.

11 Claims, No Drawings

DEXTRAN FUNCTIONALIZED BY HYDROPHOBIC AMINO ACIDS

This is a Continuation-in-Part of International Application No. PCT/IB2007/002807 filed Sep. 26, 2007, which claims the benefit of International Application No. PCT/IB2006/002666 filed Sep. 26, 2006 and French Application No. 07 02316 filed Mar. 29, 2007 and U.S. Provisional Application No. 60/907,376 filed Mar. 29, 2007. The disclosure of the prior applications is hereby incorporated by reference herein in their entirety.

The present invention relates to novel biocompatible polymers based on dextran.

These polymers can be used especially for the administration of active ingredient(s) (AI) to humans or to animals for therapeutic and/or prophylactic purposes.

The present invention relates to novel amphiphilic dextran derivatives functionalized by at least one hydrophobic alpha-amino acid. These novel dextran derivatives have good biocompatibility, and their hydrophobicity can readily be modulated without altering their biocompatibility.

Among the amphiphilic dextrans, the carboxymethyl dextrans from Biodex described in U.S. Pat. No. 6,646,120 are modified by benzylamine. That hydrophobic group does not belong to the family of the alpha-amino acids.

Dellacherie et al. have also described amphiphilic dextrans (Durand, A. et al., *Biomacromolecules* 2006, 7, 958-964) (Durand, Alain et al., *Colloid Polym. Sci.* 2006, 284, 536-545) obtained by reaction of the hydroxyl functional groups of the dextran with epoxides (phenyl glycidyl ether, 1,2-epoxyoctane or 1,2-epoxydodecane). The described amphiphilic polymers are therefore not functionalized by amino acid derivatives.

In U.S. Pat. No. 5,750,678, Bauer et al. describe dextrans functionalized by C10 to C14 fatty acids. The resulting polymers are amphiphilic but are not modified by hydrophobic amino acids.

A recent review of dextran-based functional polymers (Heinze, Thomas et al., *Adv Polym Sci* 2006, 205, 199-291) does not take into account dextran functionalized by a hydrophobic amino acid.

Accordingly, the invention relates to a dextran functionalized by at least one hydrophobic alpha-amino acid radical, designated AA, said alpha-amino acid being grafted or bonded to the dextran by a bonding arm R and a functional group F,

- R being a chain containing from 1 to 18 carbon atoms, optionally branched and/or unsaturated and containing one or more heteroatoms, such as O, N or/and S, and having at least one acid functional group,
- F being an ester, a thioester, an amide, a carbonate, a carbamate, an ether, a thioether or an amine,
- AA being a hydrophobic amino acid radical, L or D, product of the coupling between the amine of the amino acid and an acid carried by the group R.

A hydrophobic amino acid radical is understood as being the product of coupling between the amine of the amino acid and an acid carried by the group R, said dextran being amphiphilic at neutral pH.

According to the invention, the functionalized dextran can correspond to the following general formulae:

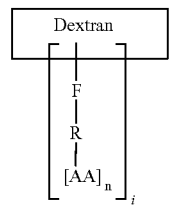

Formula I

R being a chain containing from 1 to 18 carbon atoms, optionally branched and/or unsaturated and containing one or more heteroatoms, such as O, N or/and S, and having at least one acid functional group, F being an ester, a thioester, an amide, a carbonate, a carbamate, an ether, a thioether or an amine, AA being a hydrophobic amino acid radical, L or D, product of the coupling between the amine of the amino acid and an acid carried by the group R, i represents the molar fraction of substituent F-R-[AA]n per glycoside unit and is from 0.1 to 2, n represents the molar fraction of R groups substituted by AA and is from 0.05 to 1.

When R is not substituted by AA, the acid(s) of the group R are alkaline cation carboxylates, preferably such as Na, K, said dextran being amphiphilic at neutral pH.

In an embodiment, F is an ester, a carbonate, a carbamate or an ether.

In an embodiment, the polysaccharide according to the invention is a carboxymethyl dextran (DMC) of formula IV

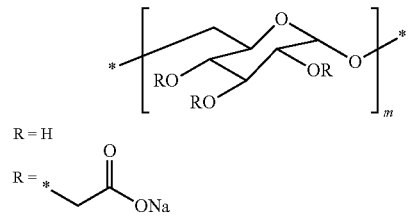

Formula IV or the corresponding acid.

In an embodiment, the polysaccharide according to the invention is a dextran monosuccinic ester or succinic acid dextran (DSA) of formula V

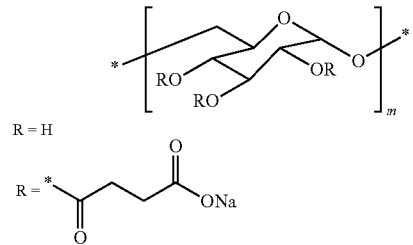

Formula V or the corresponding acid.

In an embodiment, the polysaccharide according to the invention is characterized in that the group R is selected from the following groups:

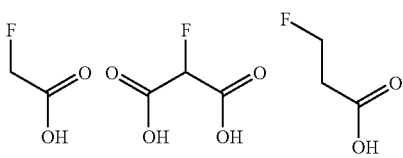

or their alkaline cation salts.

In an embodiment, the dextran according to the invention is characterized in that the hydrophobic amino acid is selected from tryptophan derivatives, such as tryptophan, tryptophanol, tryptophanamide, 2-indole ethylamine and their alkaline cation salts.

In an embodiment, the dextran according to the invention is characterized in that the tryptophan derivatives are selected from the tryptophan esters of formula II Formula II

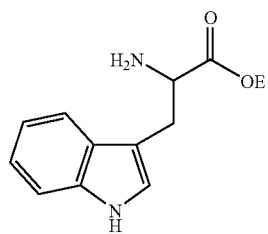

E being a group which can be:
  a linear or branched $C_1$- to $C_8$-alkyl,
  a linear or branched $C_6$- to $C_{20}$-alkylaryl or -arylalkyl.

In an embodiment, the dextran according to the invention is a carboxymethyl dextran modified by the ethyl ester of tryptophan, of formula VI:

Formula VI

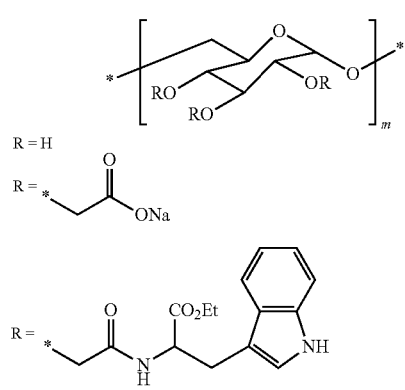

In an embodiment, the dextran according to the invention is a dextran monosuccinic ester or succinic acid dextran (DSA) modified by the ethyl ester of tryptophan, of formula VII:

Formula VII

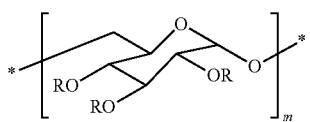

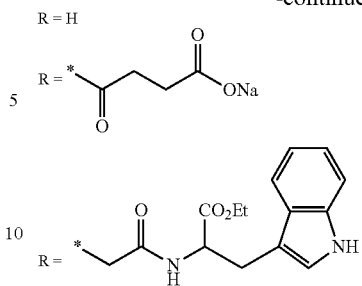

In an embodiment, the dextran according to the invention is characterized in that the hydrophobic amino acid is selected from phenylalanine, leucine, isoleucine and valine and their alcohol, amide or decarboxylated derivatives.

In an embodiment, the dextran according to the invention is characterized in that the derivatives of phenylalanine, leucine, isoleucine and valine are selected from the esters of those amino acids of formula III Formulae III

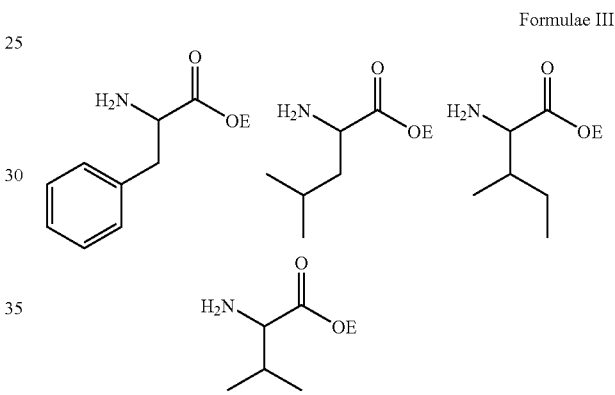

E being as defined hereinbefore.

The dextran can have a degree of polymerization m of from 10 to 10,000.

In an embodiment, it has a degree of polymerization m of from 10 to 1000.

In another embodiment, it has a degree of polymerization m of from 10 to 500.

The dextrans according to the invention are obtained by grafting an ester of the amino acid in question onto the dextran modified by a group R.

In an embodiment, an ester of formula II

Formula II

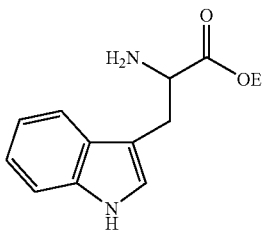

E being a group which can be:
  a linear or branched $C_1$- to $C_s$-alkyl,
  a linear or branched $C_6$- to $C_{20}$-alkylaryl or -arylalkyl is grafted onto a dextran (DMC) of formula IV

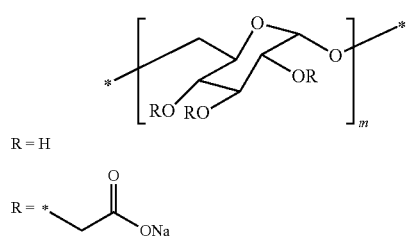

Formula IV

R = H

R = *—C(=O)—CH2—ONa

In another embodiment, an ester of formula II as defined above is grafted onto a dextran (DSA) of formula V

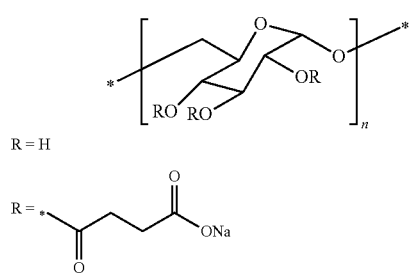

Formula V

R = H

R = *—C(=O)—CH2—CH2—C(=O)—ONa

The invention relates also to a pharmaceutical composition comprising one of the dextrans according to the invention as described hereinbefore, and at least one active ingredient.

Active ingredient is understood as being a product in the form of a single chemical entity or in the form of a combination having physiological activity. Said active ingredient can be exogenous, that is to say it is supplied by the composition according to the invention. It can also be endogenous, for example the growth factors which will be secreted in a wound during the first phase of scarring and which it will be possible to retain on said wound by means of the composition according to the invention.

The invention relates also to a pharmaceutical composition according to the invention as described hereinbefore, characterized in that it is administrable by the oral, nasal, vaginal, buccal route.

The invention relates also to a pharmaceutical composition according to the invention as described hereinbefore, characterized in that it is obtained by drying and/or lyophilization.

The invention relates also to a pharmaceutical composition according to the invention as described hereinbefore, characterized in that it is administrable in the form of a stent, a film or a coating of implantable biomaterials, in the form of an implant.

The invention relates also to a pharmaceutical composition according to the invention as described hereinbefore, characterized in that the active ingredient is selected from the group constituted by proteins, glycoproteins, peptides and non-peptide therapeutic molecules.

The possible pharmaceutical compositions are either in liquid form (nanoparticles or microparticles suspended in water or in mixtures of solvents) or in the form of a powder, an implant or a film.

In the case of local and systemic release, the possible modes of administration are by the intravenous, subcutaneous, intradermal, intramuscular, oral, nasal, vaginal, ocular, buccal route, etc.

The invention relates also to the use of the functionalized dextrans according to the invention in the preparation of pharmaceutical compositions as described hereinbefore.

EXAMPLE 1

Synthesis of a Carboxymethyl Dextran Modified by the Ethyl Ester of Tryptophan

The acid functional groups (i=1.0) of a carboxymethyl dextran having an average DP of 250 (10 g) are activated in the presence of N-methylmorpholine (4.7 g) and isobutyl chloroformate (6.4 g) in DMF (180 ml). The ethyl ester hydrochloride of tryptophan (5.4 g, Bachem) neutralized by TEA (2.0 g) in DMF (54 ml) is then grafted onto the activated polymer at 4° C. for 45 minutes. After hydrolysis of the remaining activated acids (94 ml of water), the polymer is diluted in water (720 ml) and the pH is fixed at 7 by addition of sodium hydroxide solution. The polymer is then purified by ultrafiltration. The resulting polymer has the following structure:

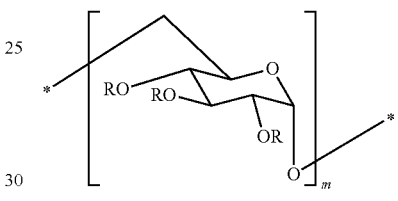

R = H or CH2COOH

1. NMM, ClCOOiBu
2. TrpOEt
3. H2O/NaOH pH 7

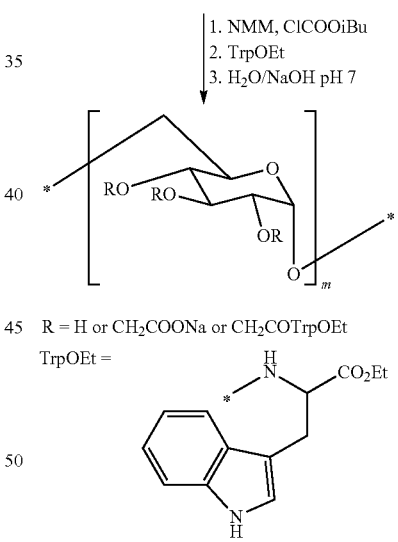

R = H or CH2COONa or CH2COTrpOEt

TrpOEt =

The molar fraction of acids modified by the ethyl ester of tryptophan is 0.45 according to $^1$H-NMR in $D_2O/NaOD$ (n=0.45). The molar fraction of unmodified acids and acids modified by a glycoside unit is 1.0 (i=1.0).

EXAMPLE 2

Synthesis of a Carboxymethyl Dextran Modified by the Methyl Ester of Leucine

The acid functional groups (i=1.0) of a carboxymethyl dextran having an average DP of 250 (10 g) are activated in the presence of N-methylmorpholine (4.7 g) and isobutyl chloroformate (6.4 g) in DMF (180 ml). The methyl ester hydrochloride of leucine (3.7 g, Bachem) neutralized by TEA (2.0 g) in DMF (54 ml) is then grafted onto the activated polymer at 4° C. for 45 minutes. After hydrolysis of the remaining activated acids (94 ml of water), the polymer is diluted in water (720 ml) and the pH is fixed at 7 by addition of sodium hydroxide solution. The polymer is then purified by ultrafiltration. The resulting polymer has the following structure:

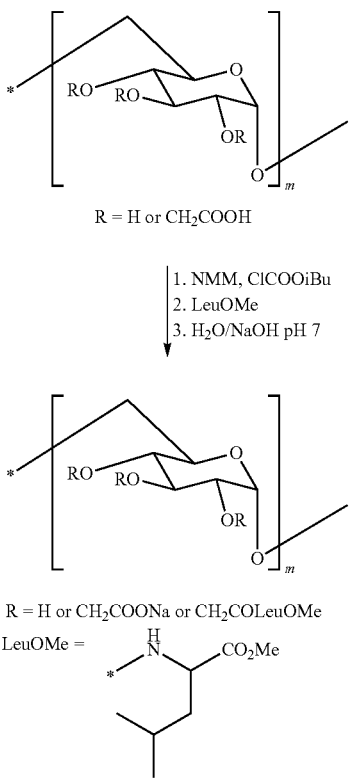

R = H or CH$_2$COOH

1. NMM, ClCOOiBu
2. LeuOMe
3. H$_2$O/NaOH pH 7

R = H or CH$_2$COONa or CH$_2$COLeuOMe

LeuOMe =

The molar fraction of acids modified by the methyl ester of leucine is 0.30 according to $^1$H-NMR in D$_2$O/NaOD (n=0.30). The molar fraction of unmodified acids and acids modified by a glycoside unit is 1.0 (i=1.0).

EXAMPLE 3

Synthesis of a Carboxymethyl Dextran Modified by the Ethyl Ester of Phenylalanine The acid functional groups (i=1.0) of a carboxymethyl dextran having an average DP of 250 (10 g) are activated in the presence of N-methylmorpholine (4.7 g) and isobutyl chloroformate (6.4 g) in DMF (180 ml). The ethyl ester hydrochloride of phenylalanine (4.6 g, Bachem) neutralized by TEA (2.0 g) in DMF (54 ml) is then grafted onto the activated polymer at 4° C. for 45 minutes. After hydrolysis of the remaining activated acids (94 ml of water), the polymer is diluted in water (720 ml) and the pH is fixed at 7 by addition of sodium hydroxide solution. The polymer is then purified by ultrafiltration. The resulting polymer has the following structure:

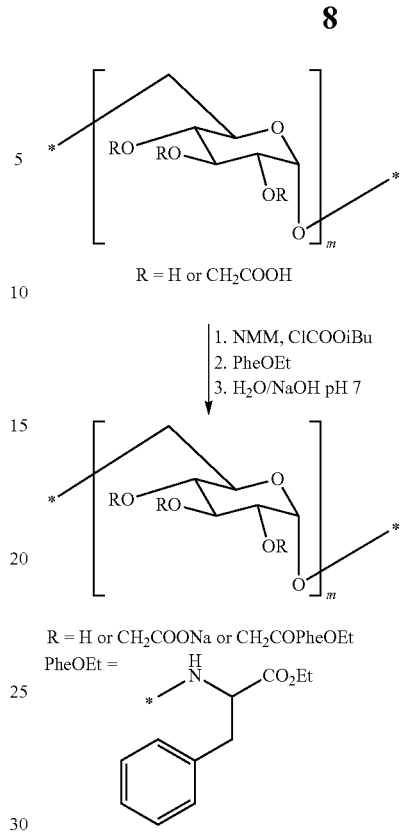

R = H or CH$_2$COOH

1. NMM, ClCOOiBu
2. PheOEt
3. H$_2$O/NaOH pH 7

R = H or CH$_2$COONa or CH$_2$COPheOEt

PheOEt =

The molar fraction of acids modified by the ethyl ester of phenylalanine is 0.45 according to $^1$H-NMR in D$_2$O/NaOD (n=0.45). The molar fraction of unmodified acids and acids modified by a glycoside unit is 1.0 (i=1.0).

EXAMPLE 4

Synthesis of a Carboxymethyl Dextran Modified by the Sodium Salt of Tryptophan

The polymer obtained in Example 1 is dissolved in water (30 mg/ml) and the pH is fixed at 12.5 by addition of 1N sodium hydroxide solution. After stirring overnight at ambient temperature, the product is purified by ultra-filtration.

The molar fraction of acids modified by the sodium salt of tryptophan is 0.45 according to $^1$H-NMR in D$_2$O (n=0.45). The molar fraction of unmodified acids and acids modified by a glycoside unit is 1.0 (i=1.0).

EXAMPLE 5

Synthesis of a Succinic Acid Dextran Modified by the Ethyl Ester of Tryptophan

The dextran having an average DP of 250, D40, (10 g, Amersham Biosciences) is dissolved in DMSO (25 ml) at 40° C. To that solution there are added succinic anhydride in solution in DMF (6.2 g in 25 ml) and N-methylmorpholine, NMM, diluted in DMF (6.2 g in 25 ml). After 1 hour's reaction, the reaction mixture is diluted in water (400 ml) and the polymer is purified by ultrafiltration. The molar fraction of succinic ester formed per glycoside unit is 1.0 according to $^1$H-NMR in D$_2$O/NaOD (i=1.0).

DSA in aqueous solution (350 g of a solution at 28 mg/ml) is acidified on ion exchange resin (300 ml of moist resin, Purolite, C100H). The resulting solution is frozen and then lyophilized.

Acidified DSA (8 g) is dissolved in DMF (115 ml) at ambient temperature. The solution is cooled to 0° C., and ethyl chloroformate (3.3 g) and then NMM (3.1 g) are added thereto. The ethyl ester hydrochloride of tryptophan (3.7 g, Bachem) neutralized by TEA (1.4 g) in DMF (37 ml) is then added to the reaction mixture at 4° C., and the mixture is stirred for 45 minutes. After hydrolysis of the remaining activated acids, the polymer is diluted in water (530 ml) and the pH is fixed at 7 by addition of sodium hydroxide solution. The polymer is then purified by ultrafiltration. The resulting polymer has the following structure:

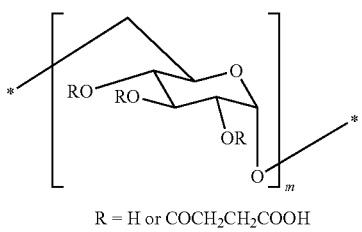

R = H or COCH$_2$CH$_2$COOH

1. NMM, ClCOOEt
2. TrpOEt
3. H$_2$O/NaOH pH 7

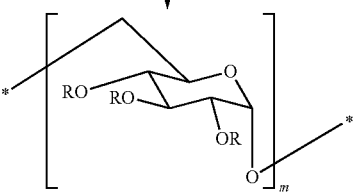

R = H or COCH$_2$CH$_2$COONa or COCH$_2$CH$_2$COTrpOEt

TrpOEt =

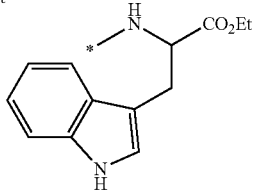

The molar fraction of acids modified by the ethyl ester of tryptophan is 0.45 according to $^1$H-NMR in D$_2$O/NaOD (n=0.45). The molar fraction of unmodified acids and acids modified by a glycoside unit is 1.0 (i=1.0).

EXAMPLE 6

Synthesis of a Succinic Acid Dextran Modified by the Ethyl Ester of Tryptophan

The dextran having an average DP of 250, D40, (20 g, Amersham Biosciences) is dissolved in DMSO (50 ml) at 40° C. To that solution there are added succinic anhydride in solution in DMF (24.7 g in 50 ml) and N-methylmorpholine, NMM, diluted in DMF (25.0 g in 50 ml). After 3 hours' reaction, the reaction mixture is diluted in water (800 ml) and the polymer is purified by ultrafiltration. The molar fraction of succinic ester formed per glycoside unit is 1.8 according to $^1$H-NMR in D$_2$O/NaOD (i=1.8).

DSA in aqueous solution (720 g of a solution at 29.5 mg/ml) is acidified on ion exchange resin (300 ml of moist resin, Purolite, C100H). The resulting solution is frozen and then lyophilized.

Acidified DSA (22.3 g) is dissolved in DMF (542 ml) at ambient temperature. The solution is cooled to 0° C., and ethyl chloroformate (13.4 g) and then NMM (12.5 g) are added thereto. The ethyl ester hydrochloride of tryptophan (7.5 g, Bachem) neutralized by TEA (2.8 g) in DMF (75 ml) is then added to the reaction mixture at 4° C., and the mixture is stirred for 45 minutes. After hydrolysis of the remaining activated acids, the polymer is diluted in water (530 ml) and the pH is fixed at 7 by addition of sodium hydroxide solution. The polymer is then purified by ultrafiltration. The resulting polymer has the following structure:

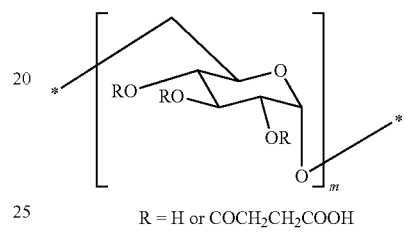

R = H or COCH$_2$CH$_2$COOH

1. NMM, ClCOOEt
2. TrpOEt
3. H$_2$O/NaOH pH 7

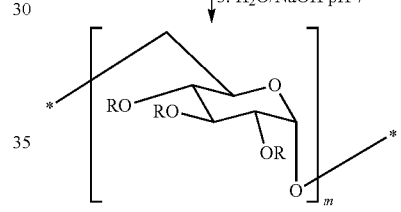

R = H or COCH$_2$CH$_2$COONa or COCH$_2$CH$_2$COTrpOEt

TrpOEt =

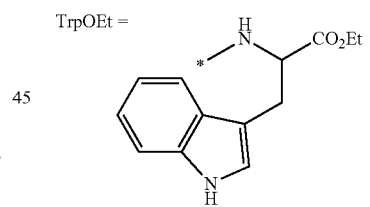

The molar fraction of acids modified by the ethyl ester of tryptophan is 0.25 according to $^1$H-NMR in D$_2$O/NaOD (n=0.25). The molar fraction of unmodified acids and acids modified by a glycoside unit is 1.8 (i=1.8).

The invention claimed is:
1. A pharmaceutical composition comprising:
(a) a functionalized dextran of the following general formula:

Formula IV

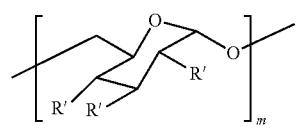

-continued

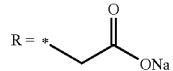

wherein:
  each R' independently represents —OH or —F—R-[AA]$_n$, a molar fraction of substituent —F—R-[AA]$_n$, per glycoside unit being from 0.1 to 2,
  m is the degree of polymerization and is from 10 to 10,000,
  R represents a chain containing from 1 to 18 carbon atoms and having at least one acid functional group prior to attachment to AA, the chain optionally being branched and/or unsaturated and optionally comprising one or more heteroatoms,
  F represents an ester, a thioester, an amide, a carbonate, a carbamate, an ether, a thioether or an amine,
  AA represents a hydrophobic amino acid radical, L- or D-isomer, derived from a coupling between an amine of an amino acid and the at least one acid functional group of R, the amino acid, prior to attachment to R, being selected from the group consisting of tryptophan, phenylalanine, leucine, isoleucine and valine, and alcohol, amide or decarboxylated derivatives thereof, and alkaline cation salts thereof,
  n represents a molar fraction of R groups substituted by AA and is from 0.05 to 1,
  when R is not substituted by AA, the acid(s) of the group R are alkaline cation carboxylates, and
  the functionalized dextran is amphiphilic at neutral pH; and
(b) at least one active ingredient selected from the group consisting of proteins, glycoproteins, peptides and non-peptide therapeutic molecules.

2. The pharmaceutical composition according to claim 1, wherein the group F is an ester, a carbonate, a carbamate or an ether.

3. The pharmaceutical composition according to claim 1, wherein, prior to attachment of the AA moiety,
  F is an ether, and
  R is —CH$_2$—COONa or the corresponding acid.

4. The pharmaceutical composition according to claim 1, wherein, prior to attachment of the AA moiety,
  F is an ester, and
  R is —CH$_2$—CH$_2$—COONa or the corresponding acid.

5. The pharmaceutical composition according to claim 1, wherein, prior to attachment of the AA moiety, F—R is selected from the group consisting of:

and alkaline cation salts thereof.

6. The pharmaceutical composition according to claim 1, wherein the hydrophobic amino acid is tryptophan, an alcohol, amide or decarboxylated derivative thereof, or an alkaline cation salt thereof.

7. The pharmaceutical composition according to claim 1, wherein the hydrophobic amino acid AA is a sodium salt of tryptophan.

8. The pharmaceutical composition according to claim 7, wherein, prior to attachment of the AA moiety,
  F is an ether, and
  R is —CH$_2$—COONa or the corresponding acid.

9. The pharmaceutical composition according to claim 1, wherein, prior to attachment of the AA moiety, R is —CH$_2$—COONa or the corresponding acid, and AA is a sodium salt of tryptophan.

10. The pharmaceutical composition according to claim 1, wherein the hydrophobic amino acid AA is selected from the group consisting of phenylalanine, leucine, isoleucine and valine and alcohol, amide and decarboxylated derivatives thereof.

11. The pharmaceutical composition according to claim 1, wherein:
  prior to attachment of the AA moiety, F is an ether, and R is —CH$_2$—COONa or the corresponding acid, and
  the AA moiety is an alkaline cation salt of phenylalanine.

* * * * *